US00PP25182P3

(12) United States Plant Patent

Klemm et al.

(10) Patent No.: US PP25,182 P3

(45) Date of Patent: Dec. 16, 2014

(54) *LOBELIA* PLANT NAMED 'KLELE12473'

(50) Latin Name: *Lobelia erinus*
Varietal Denomination: KLELE12473

(71) Applicant: Klemm+Sohn GmbH & Co. KG, Stuttgart (DE)

(72) Inventors: Nils Klemm, Stuttgart (DE); Guido Von Tubeuf, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 172 days.

(21) Appl. No.: 13/694,078

(22) Filed: Oct. 26, 2012

(65) Prior Publication Data

US 2014/0123358 P1 May 1, 2014

(51) Int. Cl.
*A01H 5/00* (2006.01)

(52) U.S. Cl.
USPC ..... Plt./451

(58) Field of Classification Search
CPC ..... A01H 5/02
USPC ..... Plt./451
See application file for complete search history.

(56) References Cited

U.S. PATENT DOCUMENTS

PP20,760 P2 * 2/2010 Giesen ..... Plt./451

* cited by examiner

*Primary Examiner* — June Hwu
(74) *Attorney, Agent, or Firm* — Jondle & Associates, P.C.

(57) ABSTRACT

A new and distinct *Lobelia* plant named 'KLELE12473' particularly distinguished by white petals with blue corolla tubes and early flowering time, is disclosed.

1 Drawing Sheet

Genus and species: *Lobelia erinus*.
Variety denomination: 'KLELE12473'.

BACKGROUND OF THE NEW PLANT

The present invention comprises a new and distinct variety of *Lobelia*, botanically known as *Lobelia erinus*, and hereinafter referred to by the variety name 'KLELE12473'. The new variety resulted from a controlled cross conducted in June 2006 in Stuttgart, Germany, between female parent *Lobelia* plant named 'LE 05 0429', (unpatented) and an unnamed male parent *Lobelia* plant. A single plant selection was subsequently chosen for further evaluation and asexual propagation.

The new variety was first propagated via vegetative cuttings and in vitro propagation in May of 2007 in Stuttgart, Germany, and has been asexually reproduced repeatedly by vegetative cuttings for 15 generations. 'KLELE12473' has been found to retain its distinctive characteristics through successive asexual propagations via vegetative cuttings.

Plant Breeder's Rights for this variety have not been applied for. 'KLELE12473' has not been made publicly available more than one year prior to filing of this application.

SUMMARY OF THE INVENTION

The following are the most outstanding and distinguishing characteristics of this new variety when grown under normal horticultural practices in a glass greenhouse in Stuttgart, Germany.

1. White petals with blue corolla tubes; and
2. Early flowering time.

DESCRIPTION OF PHOTOGRAPH

This new *Lobelia* plant is illustrated by the accompanying photograph which shows overall plant habit including blooms, buds, and foliage of the plant in full color. The colors shown are as true as can be reasonably obtained by conventional photographic procedures. The photograph was taken in spring of 2012 on a 3-month old *Lobelia* plant grown in a 10 centimeter pot in a glass pot in a glass greenhouse in Stuttgart, Germany under normal horticultural practices.

DESCRIPTION OF THE NEW VARIETY

The following detailed descriptions set forth the distinctive characteristics of 'KLELE12473'. The data which define these characteristics were collected from asexual reproductions carried out in Stuttgart, Germany. The plant history was taken in the spring of 2012 on 3-month old plants grown in 10 centimeter pots in a glass greenhouse with a pinch date at week eight. Color readings were taken under natural light. Color references are primarily to The R.H.S. Colour Chart of The Royal Horticultural Society of London (R.H.S.), Fifth Edition (2007).

DETAILED BOTANICAL DESCRIPTION OF THE NEW PLANT

Classification:
- *Botanical.*—*Lobelia erinus.*
- *Common name.*—*Lobelia.*
- *Designation.*—'KLELE12473'.

Parentage:
- *Female parent.*—*Lobelia* plant named 'LE 05 0429' (unpatented).
- *Male parent.*—Unnamed.

Growth:
- *Growth and branching habit.*—Half-hanging.
- *Form.*—Rounded to flat.

*Height* (*measured from the top of the soil, including any flowers*).—10.0 cm to 12.0 cm.
*Width* (*horizontal plant diameter, including any flowers*) .—10.0 cm to 12.0 cm.
*Time to produce a finished flowering plant.*—8 weeks.
*Outdoor plant performance*.—Very good.
*Time to initiate roots.*—3 weeks.
*Root description*.—Fine, white roots, freely branching and dense.

Leaves:
*Arrangement*.—Alternate.
*Length.*—2.0 cm.
*Width.*—0.3 cm.
*Shape*.—Elliptical to lanceolate.
*Margin*.—Serrate.
*Apex*.—Obtuse.
*Base*.—Acute.
*Texture* (*both upper and lower surfaces*).—Smooth.
*Color* (*immature and mature leaves*).—Upper surface: RHS 137A. Lower surface: RHS 137C.
*Venation*.—Pinnate.

Stems:
*Length.*—10.0 cm.
*Diameter.*—0.2 cm.
*Internode length.*—1.0 cm to 1.5 cm.
*Color*.—RHS 137B.
*Texture*.—Smooth.
*Stem anthocyanin*.—Absent.
*Peduncle*.—Color: RHS 137B. Length: 1.0 cm to 3.0 cm. Diameter: 0.05 cm. Texture: Smooth.

Flower buds:
*Color* (*when first opening*).—Bluish at the apex (RHS 97A) with yellow to greenish white at the base (RHS 150C).
*Shape*.—Inverse drop.
*Diameter.*—0.25 cm.
*Length.*—0.8 cm.

Inflorescence:
*Blooming habit*.—Continuous.
*Lastingness of individual blooms on plant*.—Approximately 1 week.
*Fragrance*.—Absent.
*Inflorescence type*.—Raceme.
*Quantity of flowers and buds per flowering branch.*—10 to 15.

Flowers:
*Arrangement*.—Flowers form at apical axils, with one flower per axil.
*Flower diameter* (*horizontal*).—1.5 cm.
*Flower height* (*vertical*).—1.0 cm.
*Immature flower*.—Upper lobes color (both upper and lower surfaces): More white than RHS NN155D. Lower lobes color: Upper surface: More white than RHS NN155D. Lower surface: More white than RHS NN155D and very slightly bluish.
*Mature flower*.—Upper lobes: Color (both upper and lower surfaces): More white than RHS NN155D. Length: 0.6 cm. Width: 0.2 cm. Shape: Obovate. Apex: Obtuse. Margin: Entire. Texture (both upper and lower surfaces): Smooth. Lower lobes: Color: Upper surface: More white than RHS NN155D. Lower surface: More white than RHS NN155D and very slightly bluish. Length: 0.9 cm. Width: 0.2 cm. Shape: Obovate. Apex: Obtuse. Margin: Entire. Texture (both upper and lower surfaces): Smooth.
*Corolla tube*.—Color (both inside and outside surfaces): RHS 96D. Tube length: 1.0 cm. Diameter: 0.25 cm.
*Calyx*.—Quantity of sepals: 5. Color (both upper and lower surfaces): RHS 138A. Length: 0.9 cm. Fused part: 0.4 cm. Non-fused part: 0.5 cm. Diameter (at fusion point): 0.1 cm. Shape: Funnel, star-shaped with fused sepals in lower half. Apex: Acute. Texture (both upper and lower surfaces): Smooth.

Reproductive organs:
*Androecium*.—Quantity of anthers: 5. Filament length: 0.9 cm. Filament color: Bluish white (RHS 97D). Pollen color: Grey. Pollen amount: Sparse.
*Gynoecium*.—Pistil length: Approximately 0.5 cm. Stigma color: Grey. Style length: 0.7 cm. Style color: RHS 142D.

Fruit and seed set: None observed.
Disease and insect resistance: Typical of species.

COMPARISON WITH PARENTAL AND COMMERCIAL VARIETIES

'KLELE12473' differs from the female parent, 'LE 05 0429' (unpatented) in that 'KLELE12473' has earlier flowering, very good branching, and weaker stems, whereas 'LE 05 0429' has later flowering, moderate branching, and stronger stems.

A comparison of 'KLELE12473' to the unnamed male parent plant cannot be provided as the unnamed male parent is not available for comparison.

'KLELE12473' differs from commercial variety 'Tech Heplib' (U.S. Plant Pat. No. 20,760) in that 'KLELE12473' has leaves with an obtuse apex and smooth texture on both surfaces, whereas 'Tech Heplib' has leaves with an acute or broadly acute apex and both surfaces covered with very short hair. Additionally, 'KLELE12473' has flower buds with an inverse drop shape, whereas 'Tech Heplib' has flower buds with an oblong shape.

We claim:

1. A new and distinct *Lobelia* plant named 'KLELE12473' as shown and described herein.

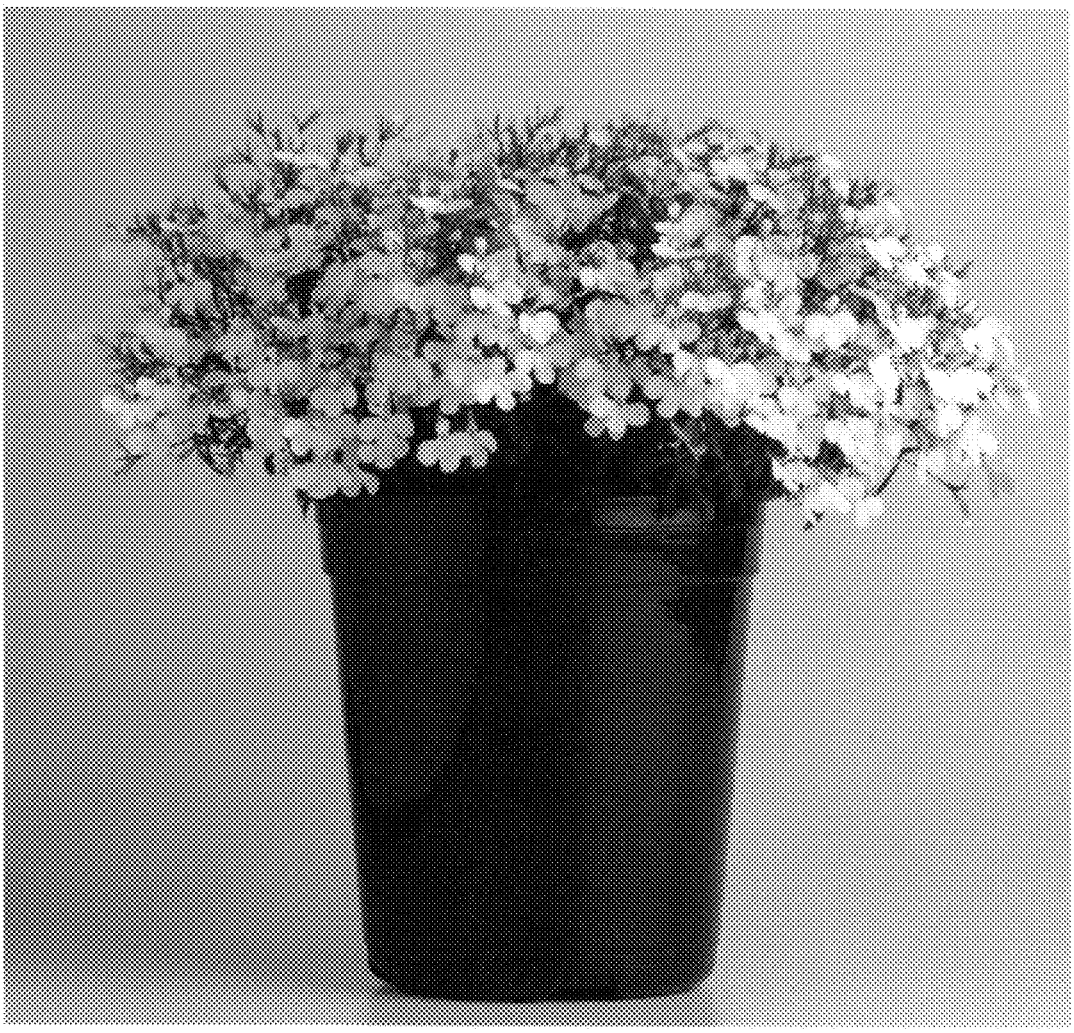

* * * * *